(12) United States Patent
Blier et al.

(10) Patent No.: US 9,706,990 B2
(45) Date of Patent: Jul. 18, 2017

(54) SURGICAL STAPLING APPARATUS

(71) Applicant: Covidien LP, Mansfield, MA (US)

(72) Inventors: Kenneth Blier, Meriden, CT (US);
Peter Hathaway, Lebanon, CT (US);
Eric Taylor, Middletown, CT (US)

(73) Assignee: Covidien LP, Mansfield, MA (US)

( * ) Notice: Subject to any disclaimer, the term of this patent is extended or adjusted under 35 U.S.C. 154(b) by 768 days.

(21) Appl. No.: 13/945,448

(22) Filed: Jul. 18, 2013

(65) Prior Publication Data
US 2013/0304097 A1     Nov. 14, 2013

Related U.S. Application Data

(60) Division of application No. 12/350,313, filed on Jan. 8, 2009, now Pat. No. 8,490,851, which is a
(Continued)

(51) Int. Cl.
| | | |
|---|---|---|
| *A61B 17/072* | (2006.01) | |
| *A61B 17/068* | (2006.01) | |
| *A61B 17/115* | (2006.01) | |
| *A61B 17/04* | (2006.01) | |
| *A61B 17/00* | (2006.01) | |

(Continued)

(52) U.S. Cl.
CPC .......... *A61B 17/068* (2013.01); *A61B 17/04* (2013.01); *A61B 17/072* (2013.01); *A61B 17/07207* (2013.01); *A61B 17/0469* (2013.01); *A61B 17/0482* (2013.01); *A61B 17/115* (2013.01); *A61B 2017/0046* (2013.01); *A61B 2017/00473* (2013.01); *A61B 2017/00477* (2013.01); *A61B 2017/07214* (2013.01); *A61B 2017/294* (2013.01); *A61B 2017/2905* (2013.01); *A61B 2017/2919* (2013.01); *A61B 2017/2927* (2013.01); *A61B 2017/2947* (2013.01); *A61B 2017/320052* (2013.01)

(58) Field of Classification Search
CPC ........... A61B 17/072; A61B 17/07207; A61B 17/07292; A61B 17/068; A61B 17/0482; A61B 17/0469; A61B 17/1114; A61B 17/115; A61B 17/1155; A61B 2017/07214; A61B 2017/00526; A61B 2017/00831; A61B 2017/07264
USPC .............. 227/19, 175.1, 176.1, 178.1, 180.1; 606/139, 143, 151, 153, 213, 219
See application file for complete search history.

(56) References Cited

U.S. PATENT DOCUMENTS

| | | |
|---|---|---|
| 3,551,987 A | 1/1971 | Wilkinson |
| 4,345,600 A | 8/1982 | Rothfuss |

(Continued)

*Primary Examiner* — Scott A. Smith

(57) ABSTRACT

A surgical device includes a loading unit having proximal and distal portions. The proximal portion of the loading unit is configured to be attached to an actuation apparatus. The surgical device further includes a flexible shaft interconnecting the proximal portion and the distal portion of the loading unit. Additionally, the surgical device has a tool assembly disposed in mechanical cooperation with the distal portion of the loading unit. The tool assembly is configured to articulate upon activation of the actuation apparatus. In a further embodiment, the surgical device includes a guiding member operatively connected to the tool assembly. The guiding member has a body and a bore extending through the body. The bore slidably receives a suture.

8 Claims, 15 Drawing Sheets

Related U.S. Application Data continuation-in-part of application No. 12/244,808, filed on Oct. 3, 2008, now Pat. No. 8,096,460.

(60) Provisional application No. 61/021,120, filed on Jan. 15, 2008.

(51) Int. Cl.
  *A61B 17/29* (2006.01)
  *A61B 17/32* (2006.01)

(56) References Cited

U.S. PATENT DOCUMENTS

| | | | |
|---|---|---|---|
| 4,473,077 | A | 9/1984 | Noiles et al. |
| 4,485,817 | A | 12/1984 | Swiggett |
| 4,610,383 | A | 9/1986 | Rothfuss et al. |
| 5,042,707 | A | 8/1991 | Taheri |
| 5,188,636 | A | 2/1993 | Fedotov |
| 5,188,638 | A | 2/1993 | Tzakis |
| 5,242,457 | A | 9/1993 | Akopov et al. |
| 5,258,008 | A | 11/1993 | Wilk |
| 5,271,543 | A | 12/1993 | Grant et al. |
| 5,330,486 | A | 7/1994 | Wilk |
| 5,383,880 | A | 1/1995 | Hooven |
| 5,395,030 | A | 3/1995 | Kuramoto et al. |
| 5,403,326 | A | 4/1995 | Harrison et al. |
| 5,405,073 | A | 4/1995 | Porter |
| 5,433,721 | A | 7/1995 | Hooven et al. |
| 5,439,156 | A | 8/1995 | Grant et al. |
| 5,452,836 | A | 9/1995 | Huitema et al. |
| 5,465,894 | A | 11/1995 | Clark et al. |
| 5,467,911 | A | 11/1995 | Tsuruta et al. |
| 5,485,952 | A | 1/1996 | Fontayne |
| 5,490,856 | A | 2/1996 | Person et al. |
| 5,518,163 | A | 5/1996 | Hooven |
| 5,518,164 | A | 5/1996 | Hooven |
| 5,540,711 | A * | 7/1996 | Kieturakis ......... A61B 17/0218 600/204 |
| 5,632,433 | A | 5/1997 | Grant et al. |
| 5,658,300 | A | 8/1997 | Bito et al. |
| 5,667,517 | A | 9/1997 | Hooven |
| 5,674,247 | A | 10/1997 | Sohn |
| 5,690,269 | A | 11/1997 | Bolanos et al. |
| 5,779,130 | A | 7/1998 | Alesi et al. |
| 5,797,927 | A | 8/1998 | Yoon |
| 5,849,023 | A | 12/1998 | Mericle |
| 5,865,791 | A * | 2/1999 | Whayne ........... A61B 17/00234 604/500 |
| 5,868,760 | A | 2/1999 | McGuckin, Jr. |
| 5,902,312 | A | 5/1999 | Frater et al. |
| 6,119,913 | A | 9/2000 | Adams et al. |
| 6,126,058 | A | 10/2000 | Adams et al. |
| 6,152,936 | A * | 11/2000 | Christy .............. A61B 17/0483 606/139 |
| 6,241,139 | B1 | 6/2001 | Milliman et al. |
| 6,241,140 | B1 | 6/2001 | Adams et al. |
| 6,258,107 | B1 | 7/2001 | Balazs et al. |
| 6,264,086 | B1 | 7/2001 | McGuckin, Jr. |
| 6,269,997 | B1 | 8/2001 | Balazs et al. |
| 6,273,897 | B1 * | 8/2001 | Dalessandro ..... A61B 17/07207 606/139 |
| 6,290,674 | B1 * | 9/2001 | Roue ................ A61B 17/00234 604/107 |
| 6,302,311 | B1 | 10/2001 | Adams et al. |
| 6,358,259 | B1 | 3/2002 | Swain et al. |
| 6,398,795 | B1 | 6/2002 | McAlister et al. |
| 6,402,780 | B2 * | 6/2002 | Williamson, IV .... A61F 2/2427 606/153 |
| 6,443,973 | B1 | 9/2002 | Whitman |
| 6,601,749 | B2 * | 8/2003 | Sullivan ........... A61B 17/07207 227/175.1 |
| 6,695,198 | B2 | 2/2004 | Adams et al. |
| 6,702,826 | B2 | 3/2004 | Liddicoat et al. |
| 6,716,233 | B1 | 4/2004 | Whitman |
| 6,755,338 | B2 | 6/2004 | Hahnen et al. |
| 6,821,282 | B2 | 11/2004 | Perry et al. |
| 7,059,331 | B2 | 6/2006 | Adams et al. |
| 7,156,863 | B2 | 1/2007 | Sonnenschein et al. |
| 7,168,604 | B2 * | 1/2007 | Milliman ............ A61B 17/1114 227/175.1 |
| 7,235,089 | B1 | 6/2007 | McGuckin |
| 7,401,722 | B2 * | 7/2008 | Hur .................... A61B 17/115 227/179.1 |
| 7,410,086 | B2 * | 8/2008 | Ortiz ................ A61B 17/07207 227/175.1 |
| 7,722,630 | B1 | 5/2010 | Stone et al. |
| 7,758,597 | B1 | 7/2010 | Tran et al. |
| 7,776,066 | B2 | 8/2010 | Onuki et al. |
| 7,942,302 | B2 * | 5/2011 | Roby .................. A61B 17/115 227/175.1 |
| 8,057,489 | B2 | 11/2011 | Stone et al. |
| 8,096,460 | B2 * | 1/2012 | Blier ................ A61B 17/07207 227/175.1 |
| 8,453,913 | B2 * | 6/2013 | Milliman ............ A61B 17/115 227/179.1 |
| 8,469,983 | B2 * | 6/2013 | Fung ................ A61B 17/0467 606/138 |
| 8,939,343 | B2 * | 1/2015 | Milliman .......... A61B 17/07207 227/175.2 |
| 2001/0056282 | A1 | 12/2001 | Sonnenschein et al. |
| 2002/0107531 | A1 * | 8/2002 | Schreck ............ A61B 17/0469 606/142 |
| 2002/0165541 | A1 | 11/2002 | Whitman |
| 2003/0009195 | A1 | 1/2003 | Field et al. |
| 2003/0045900 | A1 | 3/2003 | Hahnen et al. |
| 2004/0102804 | A1 * | 5/2004 | Chin ................ A61B 17/00008 606/190 |
| 2005/0070754 | A1 | 3/2005 | Nobis et al. |
| 2005/0187576 | A1 | 8/2005 | Whitman et al. |
| 2006/0020271 | A1 * | 1/2006 | Stewart ............. A61B 17/0057 606/139 |
| 2006/0074328 | A1 | 4/2006 | Burbank et al. |
| 2006/0089628 | A1 | 4/2006 | Whitman |
| 2007/0027456 | A1 * | 2/2007 | Gartner ............. A61B 17/0057 606/113 |
| 2007/0084898 | A1 | 4/2007 | Scirica |
| 2007/0112337 | A1 | 5/2007 | Salman et al. |
| 2007/0114261 | A1 | 5/2007 | Ortiz et al. |
| 2007/0282358 | A1 | 12/2007 | Remiszewski et al. |
| 2008/0086154 | A1 | 4/2008 | Taylor et al. |
| 2008/0097489 | A1 * | 4/2008 | Goldfarb ................ A61B 50/30 606/151 |
| 2008/0119871 | A1 | 5/2008 | Brock et al. |
| 2008/0262492 | A1 | 10/2008 | Lee |
| 2009/0082797 | A1 * | 3/2009 | Fung ................ A61B 17/0467 606/170 |
| 2009/0090764 | A1 | 4/2009 | Viola |
| 2009/0272783 | A1 | 11/2009 | Crainich et al. |
| 2010/0048988 | A1 | 2/2010 | Pastorelli et al. |
| 2012/0037686 | A1 | 2/2012 | Hessler |

\* cited by examiner

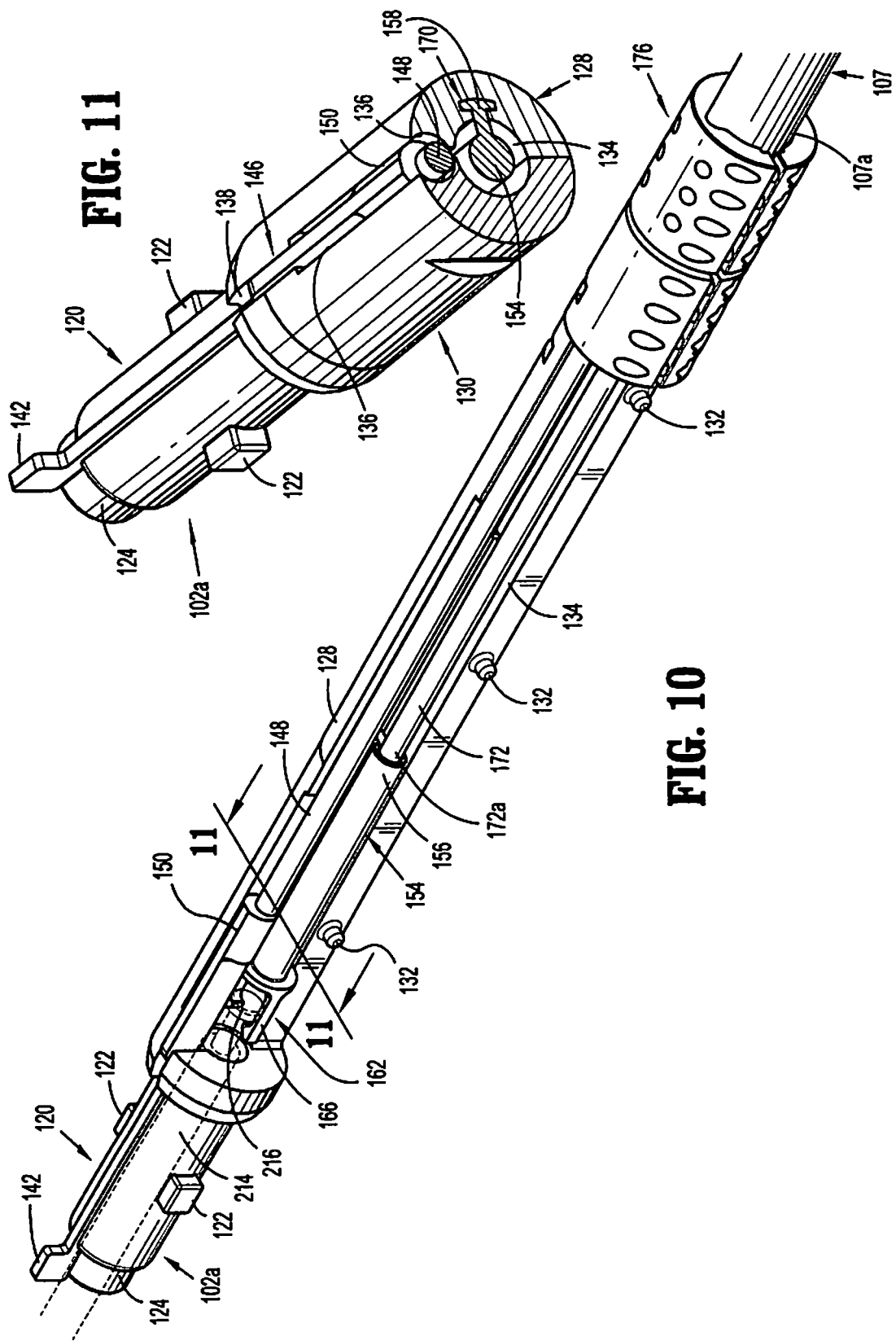

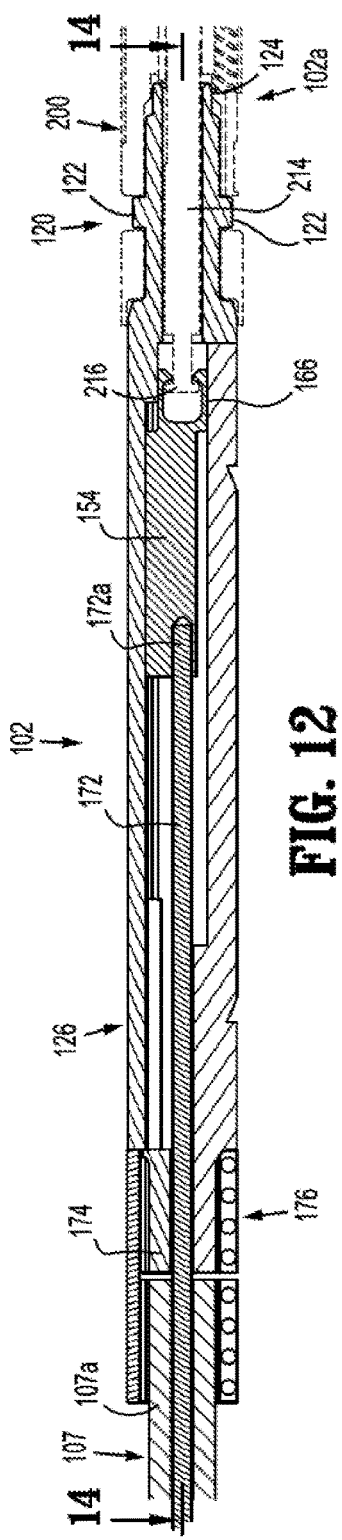

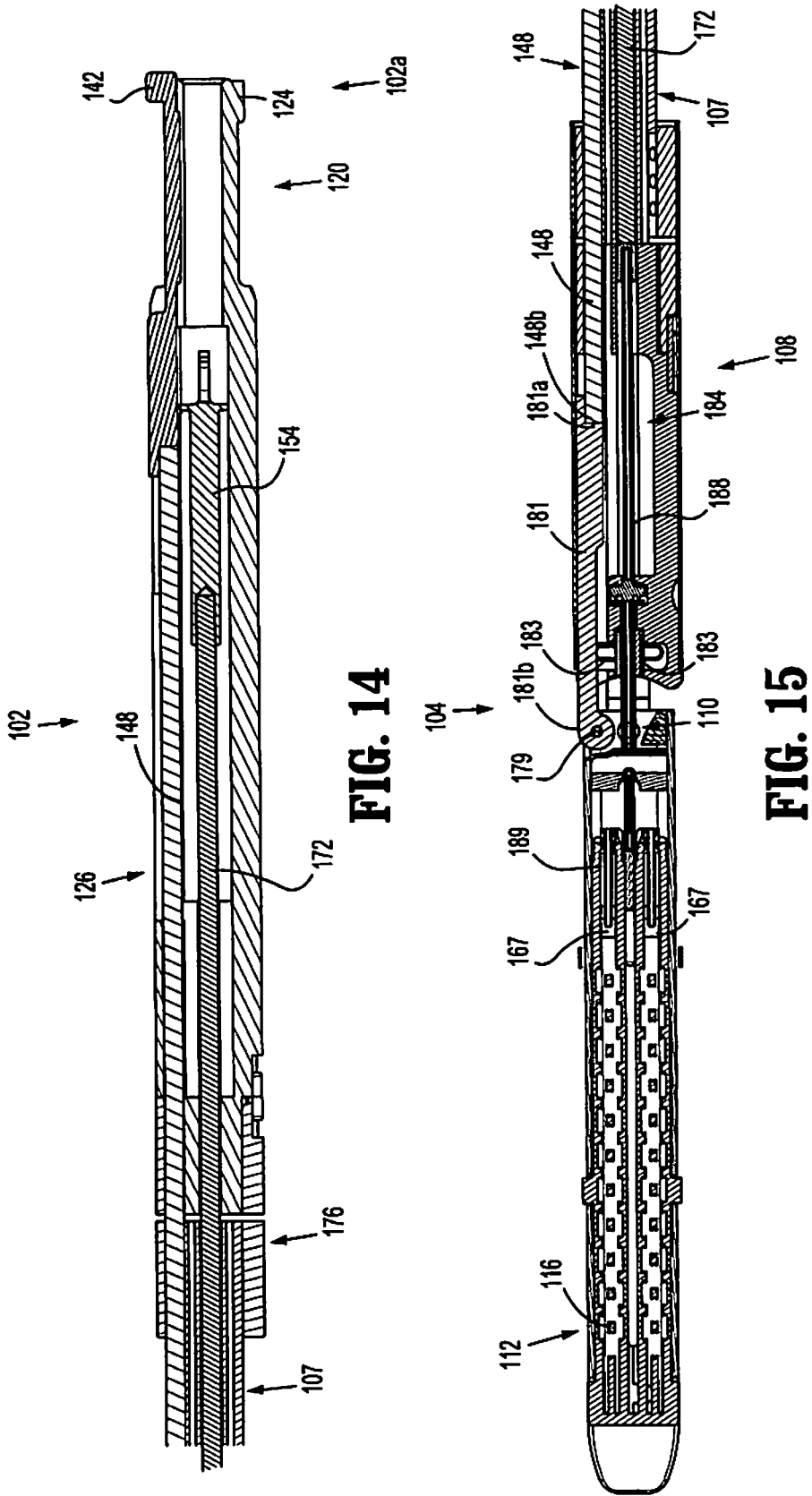

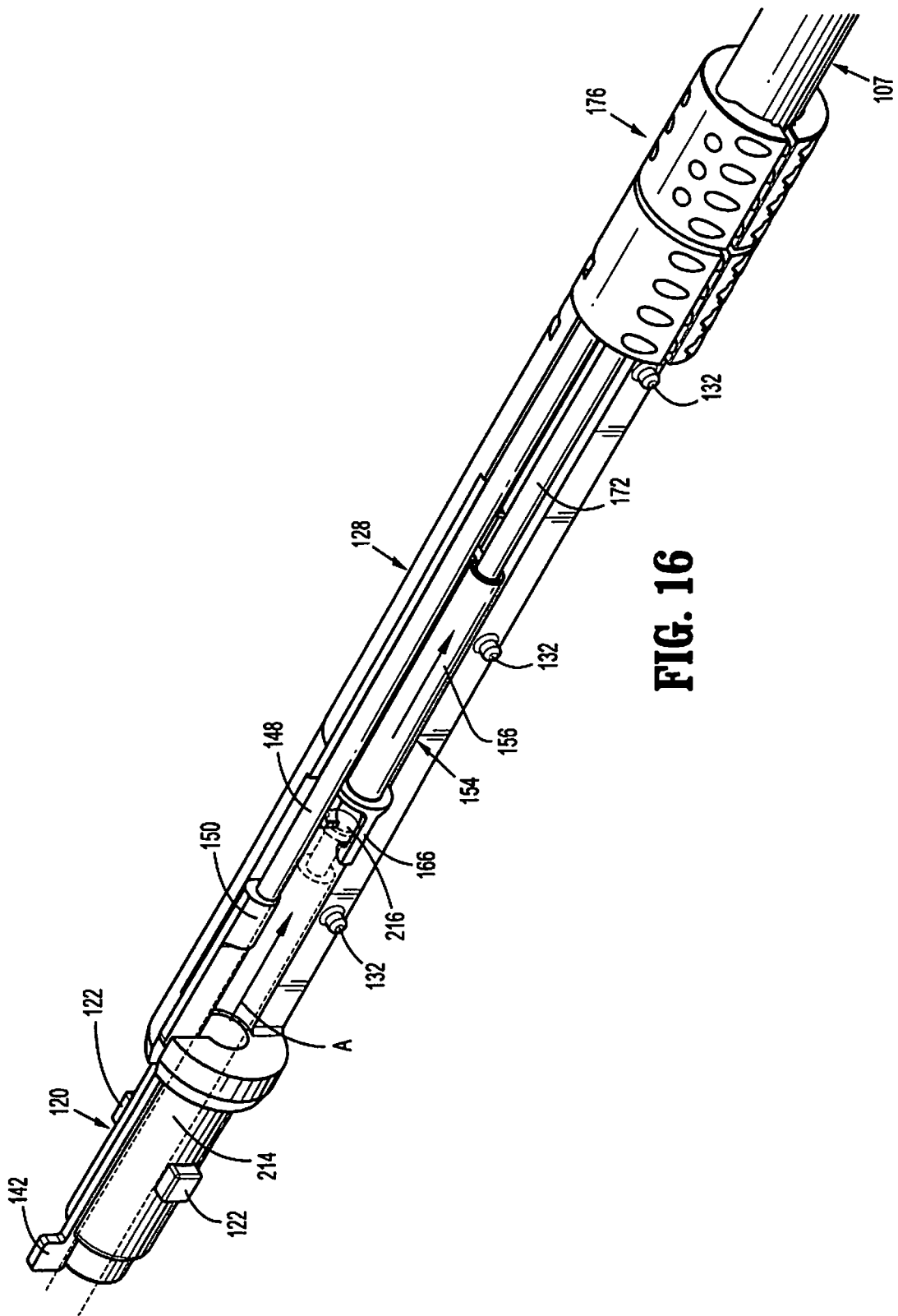

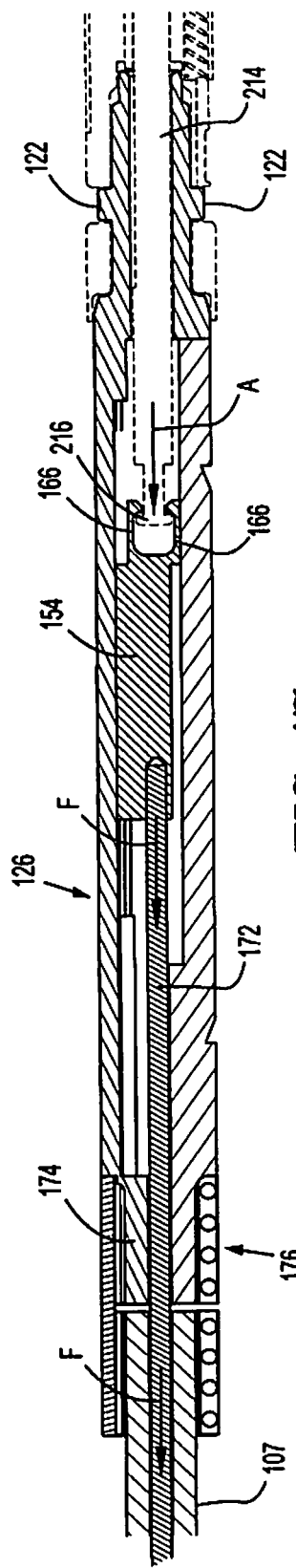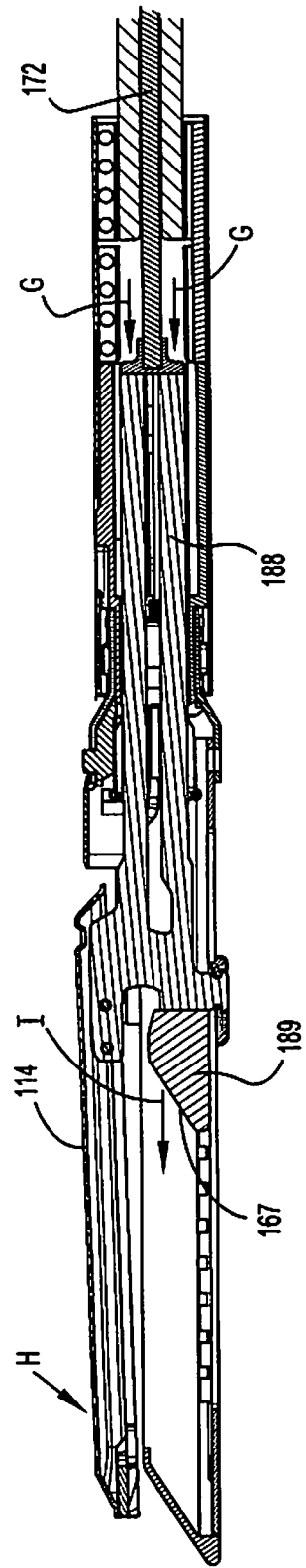

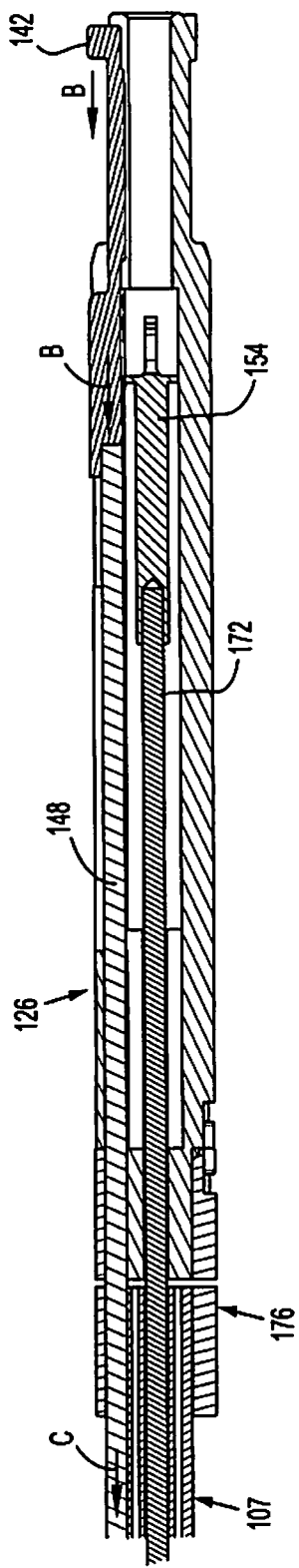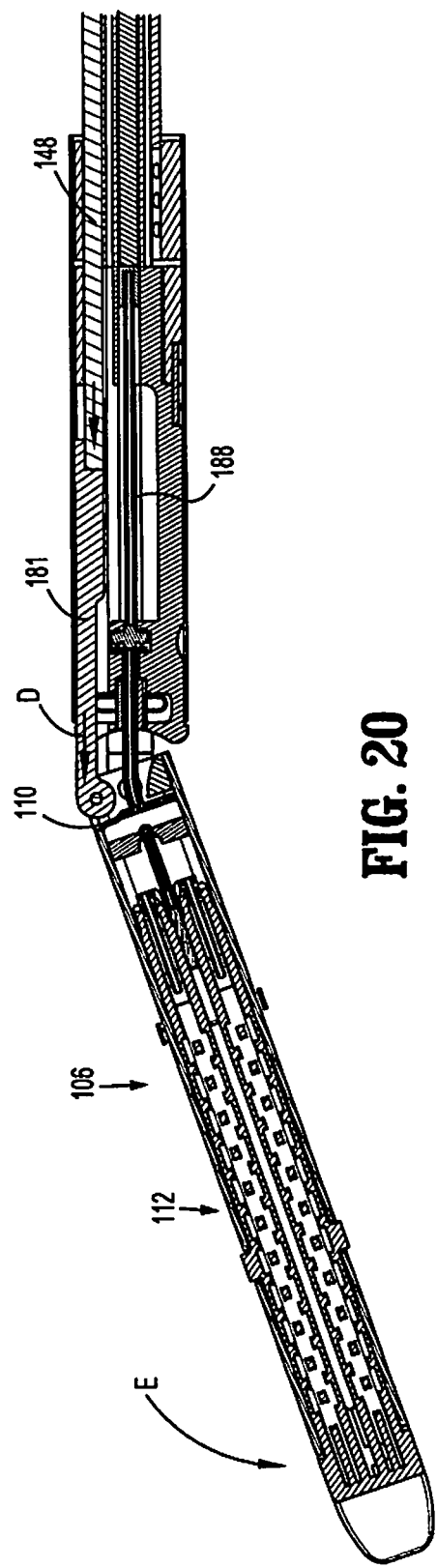

SURGICAL STAPLING APPARATUS

CROSS-REFERENCE TO RELATED APPLICATION

This application is a divisional of U.S. patent application Ser. No. 12/350,313, filed Jan. 8, 2009, now U.S. Pat. No. 8,490,851 which is a continuation-in-part of U.S. patent application Ser. No. 12/244,808, filed Oct. 3, 2008, now U.S. Pat. No. 8,096,460, which claims the benefit of and priority to U.S. Provisional Patent Application No. 61/021,120, filed Jan. 15, 2008, the entire content of each of the applications identified above being incorporated by reference herein.

BACKGROUND

1. Technical Field

The present disclosure relates to apparatus and methods for fastening tissue. More particularly, the present disclosure relates to a surgical stapling apparatus having a loading unit capable of applying surgical staples to tissue.

2. Description of Related Art

Surgical instruments for fastening tissue are well known. Some surgical fastening instruments have a tool assembly including opposing jaw structures for grasping tissue. These instruments often include a knife for incising the fastened tissue. The knife is usually positioned in one of the opposing jaw structures. At least one of the opposing jaw structures contains fasteners. These fasteners can be surgical staples or two-part fasteners.

Typically, the tool assembly includes a staple cartridge and an anvil. The staple cartridge houses a plurality of staples arranged in at least two laterally spaced rows, whereas the anvil usually includes a plurality of staple forming pockets for receiving the legs of the staples. The staple forming pockets of the anvil deform the staple legs as the staples are driven from the cartridge. A drive member located within the cartridge drives staples toward the anvil.

During the stapling operation, the drive member advances cam wedges longitudinally through the staple cartridge. The cam wedges act upon staple pushers to sequentially eject the staples from the staple cartridge. A knife may travel between the staple rows to longitudinally cut the stapled tissue between the rows of staples.

The described stapling process is frequently performed during minimally invasive surgical procedures, such as laparoscopic and endoscopic procedures. In laparoscopic and endoscopic procedures, healthcare professionals perform surgical procedures through a small incision or cannula inserted through a small entrance wound in a patient. To address the specific needs of endoscopic and laparoscopic surgical procedures, medical devices manufacturers have developed endoscopic surgical stapling instruments specifically suited to facilitate access to an operative site. Some endoscopic surgical stapling instruments include an articulatable tool assembly disposed on the distal end of the surgical stapling instrument. These surgical stapling instruments normally include an actuation apparatus to control the articulation of the tool assembly. U.S. Patent Application Serial No. 2007/0084898, which is hereby incorporated by reference in its entirety, describes a surgical stapling apparatus with an articulable tool assembly.

SUMMARY

A surgical device includes a loading unit having proximal and distal portions. The proximal portion of the loading unit is configured to be attached to an actuation apparatus. The surgical device further includes a flexible shaft interconnecting the proximal portion and the distal portion of the loading unit. Additionally, the surgical device has a tool assembly disposed in mechanical cooperation with the distal portion of the loading unit. The tool assembly is configured to articulate upon activation of the actuation apparatus. In one embodiment, the tool assembly includes an anvil assembly and a cartridge assembly. The anvil assembly is configured to move relative to the cartridge assembly upon activation of the actuation apparatus. The surgical device may further include a center rod extending through the flexible shaft and at least a section of the proximal portion of the loading unit. The center rod is operatively associated with the tool assembly. Additionally, the surgical device may have a flexible articulation rod extending alongside the flexible shaft and through at least a section of the proximal portion of the loading unit. The flexible articulation rod is operatively associated with the tool assembly. The proximal portion of the loading unit may include a housing encompassing at least a portion of the center rod and at least a portion of the flexible articulation rod.

In a further embodiment, the surgical device includes a guiding member operatively connected to the tool assembly. The guiding member has a body and a bore extending through the body. The bore slidably receives a suture

BRIEF DESCRIPTION OF THE DRAWINGS

Various embodiments of the presently disclosed surgical stapling instrument are described herein with reference to the drawings:

FIG. 10 is a perspective view of the proximal portion of the loading unit of FIG. 1 without the cover;

FIG. 11 is a perspective cross-sectional view of the proximal portion of the loading unit of FIG. 1 taken along section line 11-11 of FIG. 10;

FIG. 12 is a cross-sectional side view of the proximal portion of the loading unit of FIG. 1 taken along section line 12-12 of FIG. 4;

FIG. 13 is a cross-sectional side view of the distal portion of the loading unit of FIG. 1 taken along section line 13-13 of FIG. 3;

FIG. 14 is a cross-sectional top view of the proximal portion of the loading unit of FIG. 1 taken along section line 14-14 of FIG. 12;

FIG. 15 is a cross-sectional top view of the distal portion of the loading unit of FIG. 1 taken along section line 15-15 of FIG. 13;

FIG. 16 is a perspective view of the proximal portion of the loading unit of FIG. 1 without the cover;

FIG. 17 is cross-sectional side view of the proximal portion of the loading unit of FIG. 1;

FIG. 18 is a cross-sectional side view of the distal portion of the loading unit of FIG. 1 with a tool assembly in a clamped position;

FIG. 19 is a cross-sectional top view of the proximal portion of the loading unit of FIG. 1;

FIG. 20 is a cross-sectional top view of the distal portion of the loading unit of FIG. 1;

DETAILED DESCRIPTION

Figure 1:
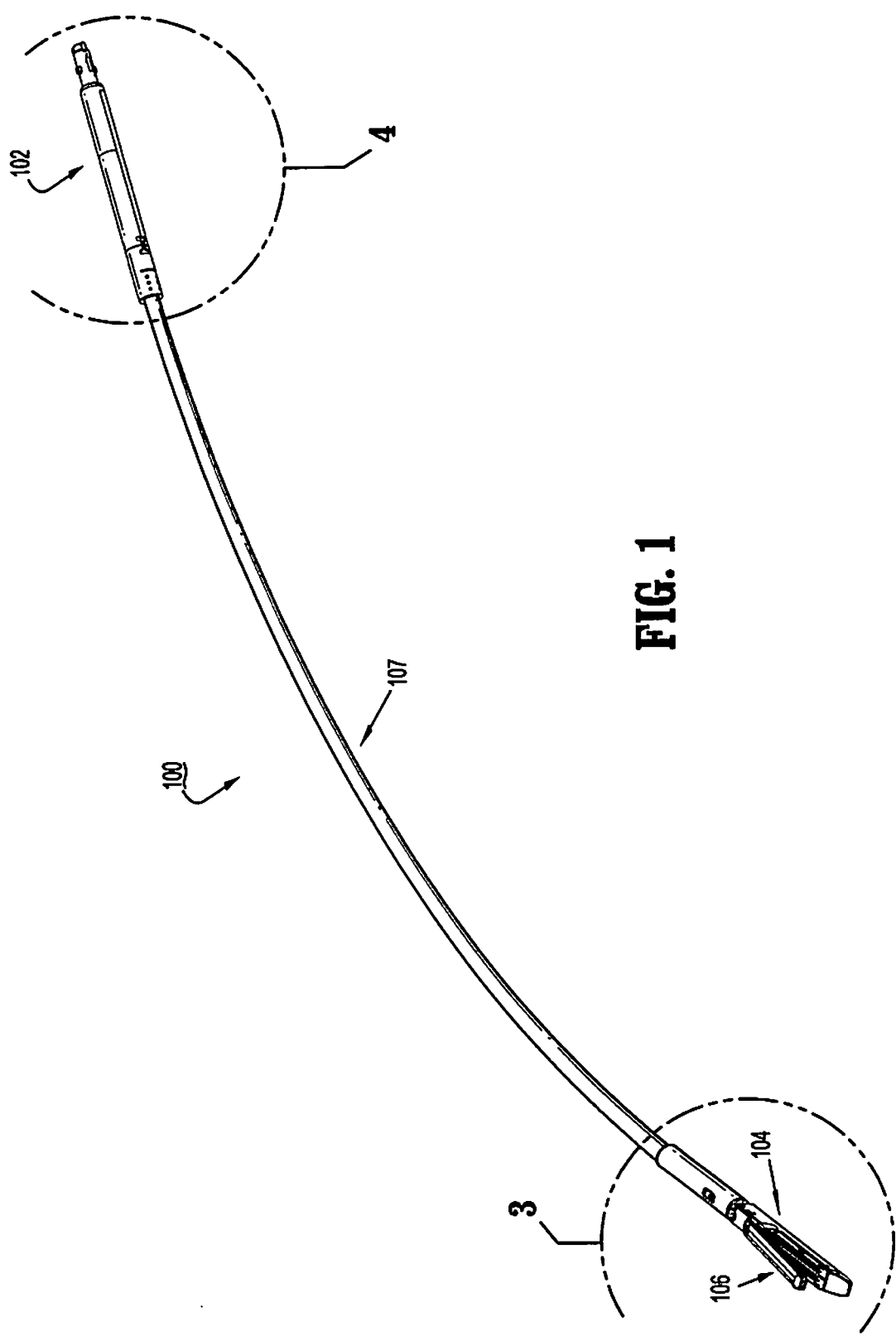
FIG. 1 is a perspective view of a loading unit of a surgical stapling instrument in accordance with an embodiment of the present disclosure.

Embodiments of the presently disclosed surgical stapling instrument will now be described in detail with reference to the drawings in which like reference numerals designate identical or corresponding elements in each of the several views. In the description that follows, the term "proximal," as is traditional, will refer to the end of the surgical stapling instrument that is closest to the operator, while the term "distal" will refer to the end of the instrument that is farthest from the operator.

Figure 2:
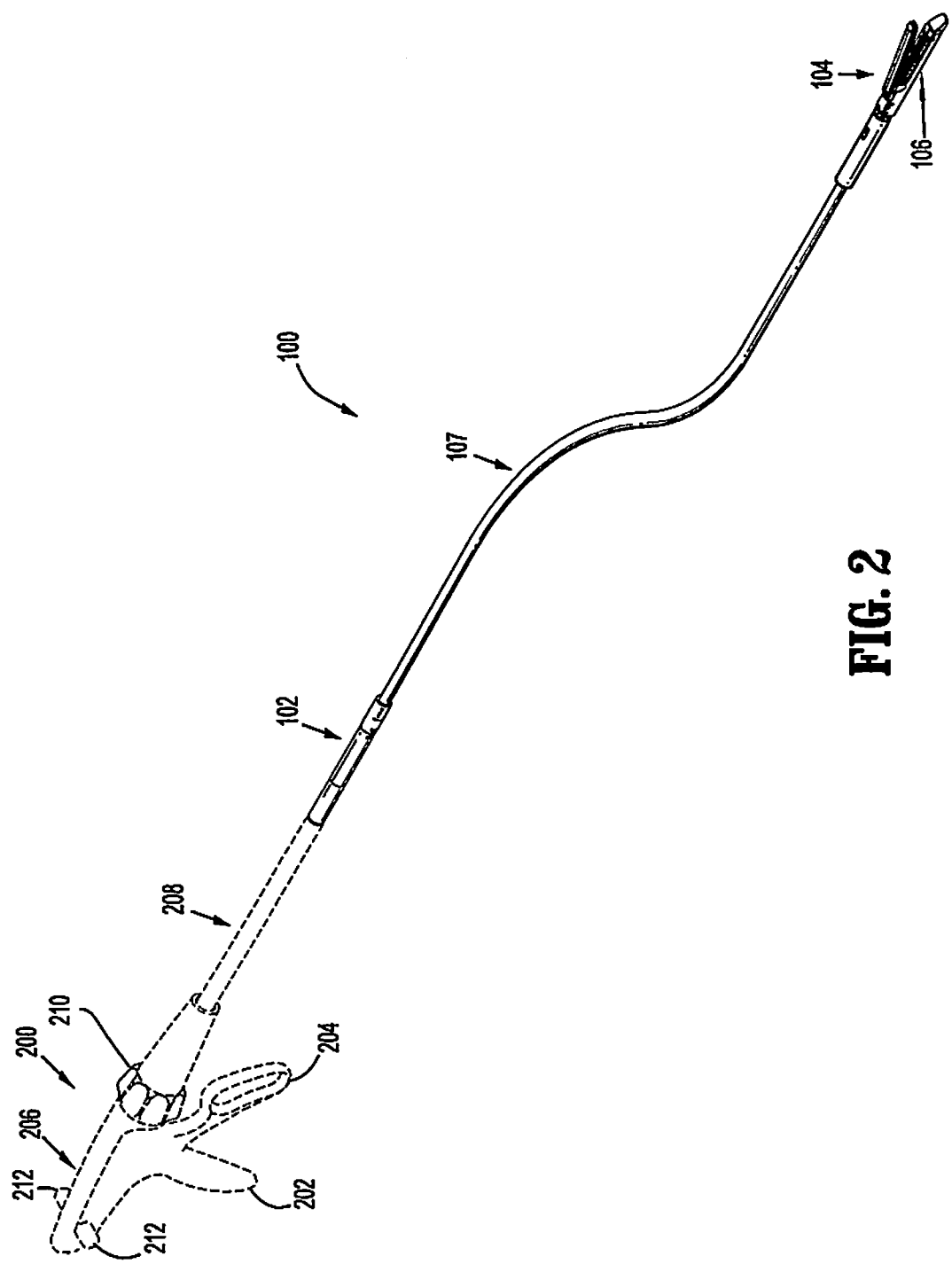
FIG. 2 is a perspective view of a surgical stapling instrument according to an embodiment of the present disclosure.

With reference to FIGS. 1 and 2, an embodiment of a loading unit of a surgical stapling instrument is generally shown as 100. Loading unit 100 may be, among other things, a single loading unit ("SULU") or a disposable loading unit ("DLU") and includes a proximal portion 102 and a distal portion 104. A flexible shaft 107 interconnects proximal portion 102 and distal portion 104. Distal portion 104 of loading unit 100 has a tool assembly 106 adapted to apply fasteners to tissue. Proximal portion 102 of loading unit 100 is configured to be releasably secured to any suitable actuation apparatus capable of actuating tool assembly 106.

In the embodiment depicted in FIG. 2, a handle assembly 200 (shown in phantom) functions as an actuation apparatus. Handle assembly 200 includes a stationary handle 202, a movable handle 204, a barrel portion 206, and an elongate body 208. During operation, movable handle 204 moves relative to stationary handle 202. The motion of movable handle 204 actuates tool assembly 106. In addition to movable handle 204, handle assembly 200 has a rotatable member 210 operatively coupled to elongate body 208, such that the rotation of rotatable member 210 causes the corresponding rotation of elongate body 208. Rotatable member 210 is rotatably mounted to barrel portion 206. Barrel portion 206 also supports a pair of retraction knobs 212 configured to move therealong. The proximal translation of retraction knobs 212 moves tool assembly 106 from an actuated positioned to a retracted position, as described in detail in U.S. Patent Application Serial No. 2007/0084898, which entire contents is hereby incorporated by reference. Handle assembly 200 may further include an articulation lever (not shown) adapted to articulate tool assembly 106.

Although the drawings show handle assembly 200, one skilled in the art will recognize that loading unit 100 may be used in conjunction with any suitable actuation apparatus capable of actuating and articulating the tool assembly 106 positioned on distal portion 104 of loading unit 100.

Figure 3:
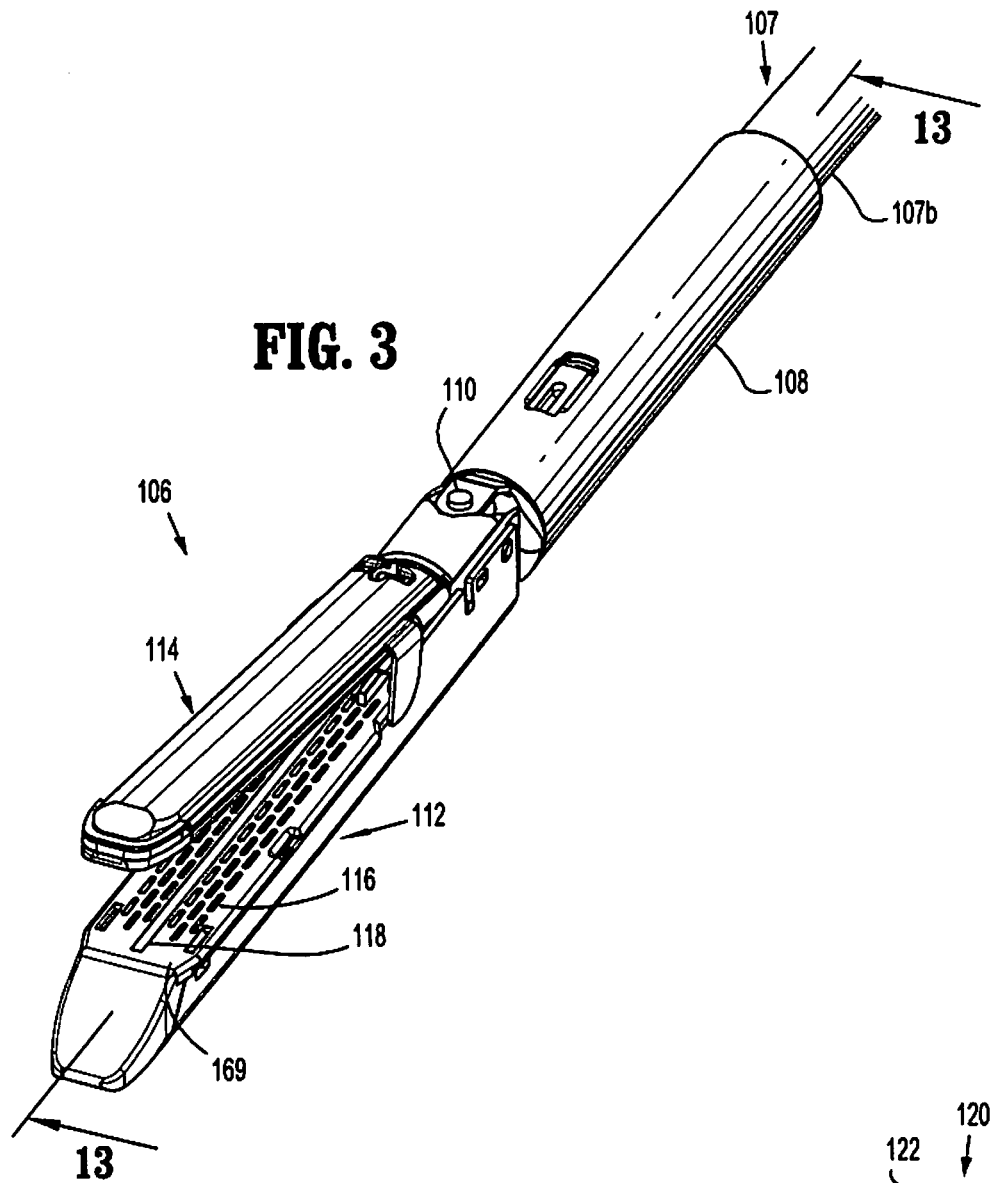
FIG. 3 is a perspective view of a distal portion of the loading unit of FIG. 1.
Figure 4:
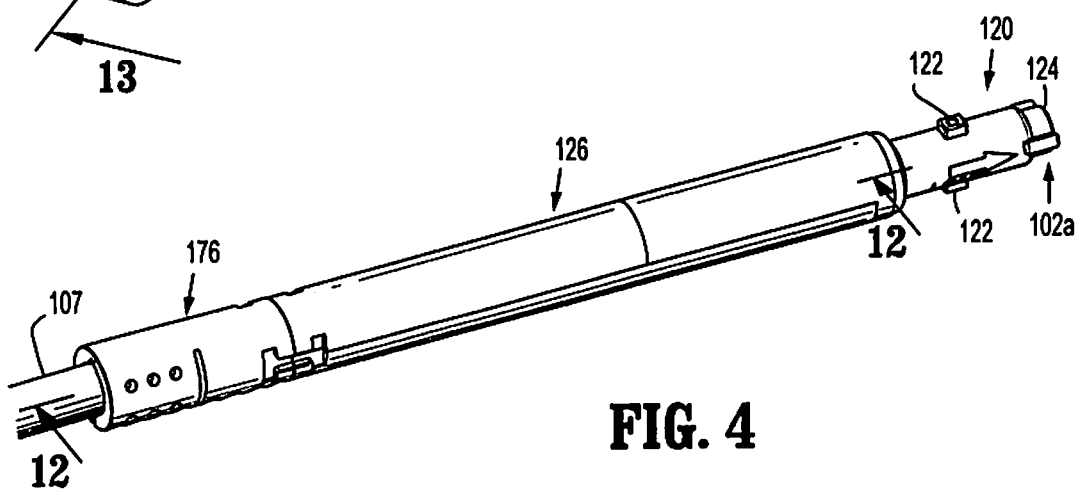
FIG. 4 is a perspective view of a proximal portion of the loading unit of FIG. 1.

Referring to FIG. 3, distal portion 104 of loading unit 100 includes a proximal body 108 and tool assembly 106. Proximal body 108 supports a distal end 107b of flexible shaft 107. A pivot member 110 pivotably connects proximal body 108 and tool assembly 106. Tool assembly 106 contains a cartridge assembly 112 and an anvil assembly 114. Cartridge assembly 112 houses a plurality of fasteners, such as staples. Anvil assembly 114, in turn, is movable in relation to cartridge assembly 112 between an open position and a clamped position. In the open position, anvil assembly 114 is spaced apart from cartridge assembly 112, as seen in FIG. 13. In the clamped position, anvil assembly 114 is in juxtaposed alignment with cartridge assembly 112, as shown in FIG. 18. Additionally, cartridge assembly 112 includes retention slots 116 adapted to receive fasteners. In one embodiment, retention slots 116 are arranged in longitudinal rows. A channel 118 adapted to receive a cutting tool may be disposed between two longitudinal rows of retention slots 116. In operation, the cutting tool moves along channel 118 in response to the actuation of an actuation apparatus, such as handle assembly 200.

Figure 3A:
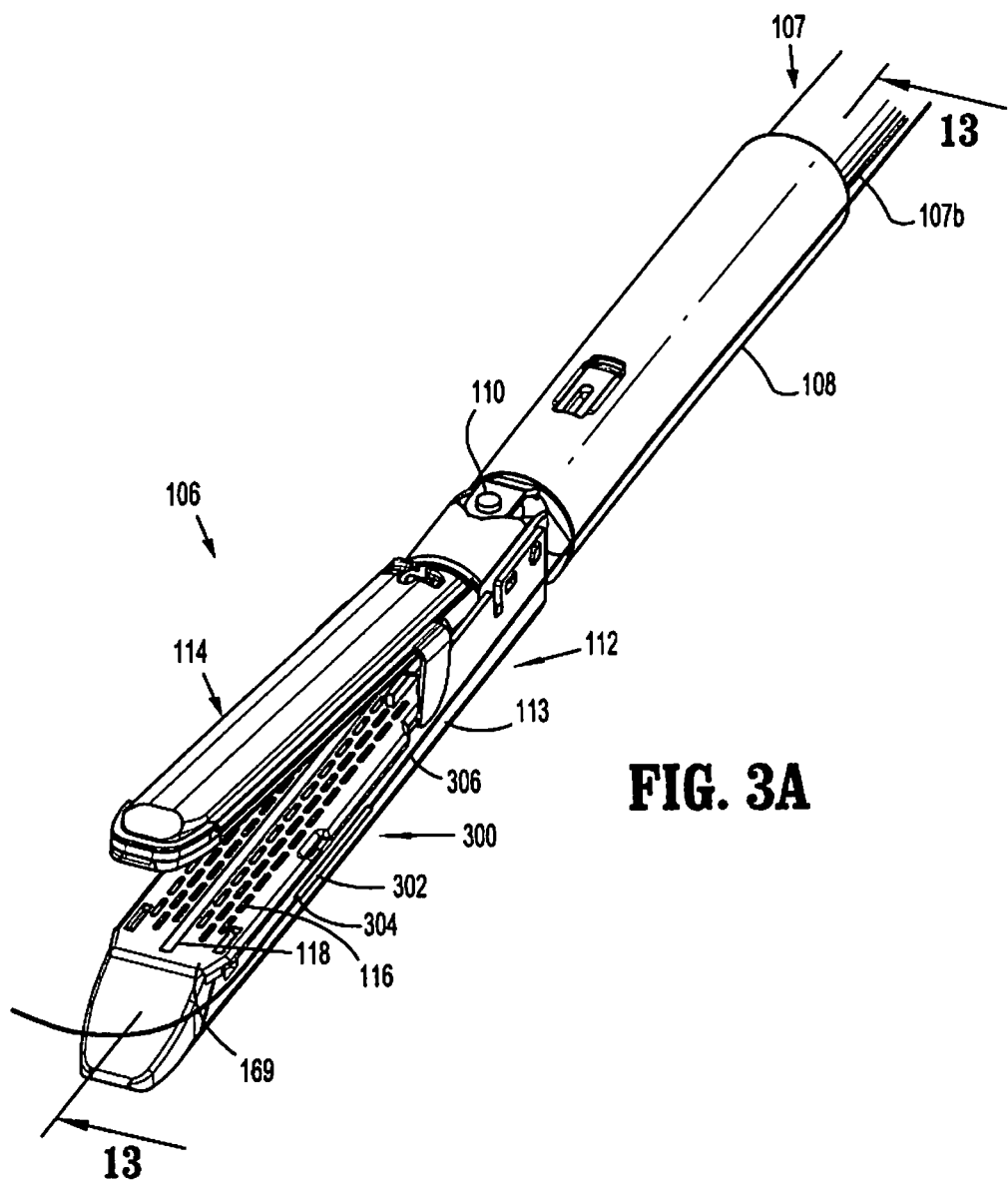
FIG. 3A is a perspective view of a distal portion of the loading unit of FIG. 1 with a guiding member.

With reference to FIG. 3A, in one embodiment, tool assembly 106 includes a guiding member 300 attached to a lateral wall 113 of cartridge assembly 112. Guiding member 300 may be secured to lateral wall 113, or any other suitable part of loading unit 100, utilizing any suitable fastening technique such as welding, crimping, or adhesives. Guiding member 300 has a substantially cylindrical body 302 and a bore 304 extending threrethrough. Bore 304 is adapted to receive a suture 306. Although the drawings show a guiding member 300 having a cylindrical shape, guiding member 300 may have any configuration, insofar as it is capable of guiding a suture therethrough. Body 302 may be made of plastic, metal, or any other suitable material. Since a portion of suture 306 is slidably positioned within bore 304 of body 302, during operation, guiding member 300 and suture 306 jointly guide the movement of loading unit 100 into the desired surgical site. While the present disclosure discusses the use of guiding member 300 in conjunction with loading unit 100, it is contemplated that that guiding member 300 may be utilized to any other suitable surgical instrument.

With reference to FIGS. 4, 9, 10, 11, 12 and 14, the proximal portion 102 of loading unit 100 is releasably secured to an actuation apparatus, as previously discussed. In particular, proximal portion 102 includes an engagement section 120 disposed at a proximal end 102a thereof. Engagement section 120 has engagement lugs 122 for releasably engaging a portion of an actuation apparatus in a bayonet coupling type fashion, as illustrated in FIG. 12. Besides engagement lugs 122, engagement section 120 includes an insertion tip 124 for facilitating insertion of engagement section 120 into a portion of an actuation apparatus and a slit 140 for receiving an articulation component 142. Slit 140 extends along the length of engagement section 120. Articulation component 142, which is slidably disposed in slit 140, may be operatively associated with any suitable articulation mechanism of an actuation apparatus. Another portion of the actuation apparatus may be inserted through a lumen 144 defined in engagement section 120. Lumen 144 extends through the length of engagement section 120 and is adapted to receive a portion of an actuation apparatus, such as an actuation shaft 214, as seen in FIG. 12. Since loading unit 100 is designed to work in conjunction with several types of actuation apparatus, engagement section 120 may have other elements suitable to engage other kinds of actuation apparatus.

Proximal portion 102 of loading unit 100 further includes an elongate member 126 connected to engagement section 120. Elongate member 126 includes a housing 128 and a cover 130. Housing 128 has engagement protrusions 132 adapted to engage cover 130. Cover 130 is detachably connected to housing 128. Housing 128 and cover 130 together form a first bore 134, a second bore 136, and a slot 138. Slot 138 extends along a proximal segment 146 and is disposed in communication with slit 140. A portion of articulation component 142 is slidably positioned in slot 138.

Second bore 136 is disposed in communication with slot 138 and is adapted to slidably receive a portion of articulation component 142. A flexible articulation rod 148 is operatively coupled to articulation component 142. In one embodiment, articulation component 142 includes an attaching portion 150 having a longitudinal opening 152. Longitudinal opening 152 is configured for supporting a portion of flexible articulation rod 148. Although shown as a solid rod, it is contemplated herein that the flexible articulation rod can be in the form of a tube and can have a variety of cross-sectional shapes including, but not limited to circular, square, etc. It is further contemplated that the articulation rod may extend alongside or on axis with the flexible shaft. Alternatively, multiple articulation rods can be positioned alongside the axis of the stapler. A section of flexible articulation rod 148 is slidably disposed in second bore 136. Second bore 136 extends through elongate member 126 and is adapted to slidably receive at least a portion of articulation component 142 and flexible articulation rod 148.

First bore 134 also extends through elongate member 126. A locking member 154 is slidably positioned in a portion of first bore 134. Therefore, first bore 134 is adapted to slidably receive locking member 154. Locking member 154 is configured to hold a portion of an actuation apparatus. In an embodiment, locking member 154 holds a distal protrusion 216 of actuation shaft 214, as seen in FIGS. 10 and 12. The locking member 154 of the depicted embodiment has an oblong body 156 including a longitudinal flange 158, a longitudinal hole 160, and a locking portion 162. Locking portion 162 is positioned at the proximal end 164 of oblong body 156 and includes a pair of legs 166. Legs 166 define a recess 168 therebetween. Each leg 166 has an elongated retaining protrusion 166a having a tapered end. In the depicted embodiment, distal protrusion 216 of actuation shaft 214 fits into recess 168 of locking portion 162. To connect distal protrusion 216 to locking member 154, a user simply has to press distal protrusion 216 against locking member 154. The pressure exerted by the user eventually forces distal protrusion 216 of actuation shaft 214 into recess 168 of locking member 154.

As previously discussed, locking member 154 additionally includes a longitudinal flange 158. Longitudinal flange 158 protrudes from a periphery of oblong body 156 and is adapted to slidably fit into a groove 170 of housing 128. Groove 170 extends along an inner surface of housing 128 and is longitudinally aligned with first bore 134.

Aside from longitudinal flange 158, locking member 154 has a longitudinal hole 160 configured to receive a flexible center rod 172. Specifically, longitudinal hole 160 supports a proximal end 172a of flexible center rod 172. Flexible center rod 172 is slidably disposed in first bore 134. Therefore, first bore 134 slidably receives at least a portion of locking member 154 and flexible center rod 172. In addition, first bore 134 is disposed in communication with lumen 144 of engagement section 120 and extends through elongate member 126.

Elongate member 126 further includes an insertion portion 174 positioned at a distal end thereof. In particular, housing 128 and cover 130 of elongate member 126 together form insertion portion 174. Insertion portion 174 facilitates insertion of elongate member 126 into a coupling 176. Coupling 176 connects elongate member 126 and flexible shaft 107. In an embodiment, coupling 176 includes a bore 178 extending therethrough. Bore 178 of coupling 176 is designed to receive insertion portion 174 of elongate member 126, a proximal end 107a of flexible shaft 107, and a portion of flexible articulation rod 148.

Figure 5:
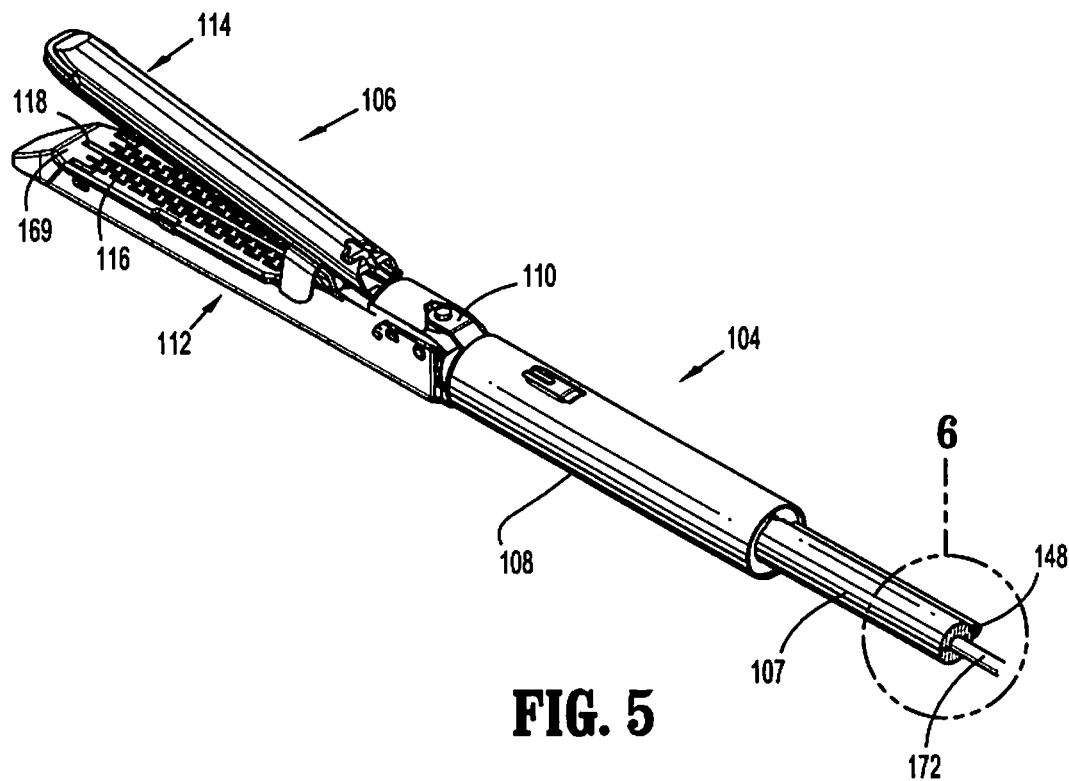
FIG. 5 is a perspective view of the flexible articulation rod, the flexible center rod, the flexible shaft, and the distal portion of the loading unit of FIG. 1.
Figure 6:
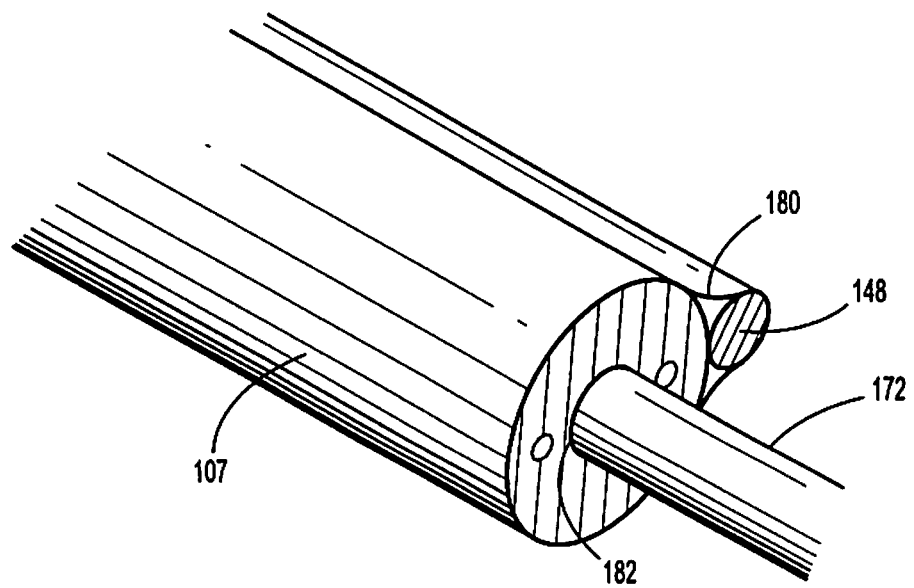
FIG. 6 is a perspective sectional view of the flexible center rod, the flexible articulation rod, and the flexible shaft of the loading unit of FIG. 1 taken around section 6 of FIG. 5.
Figures 7, 8:
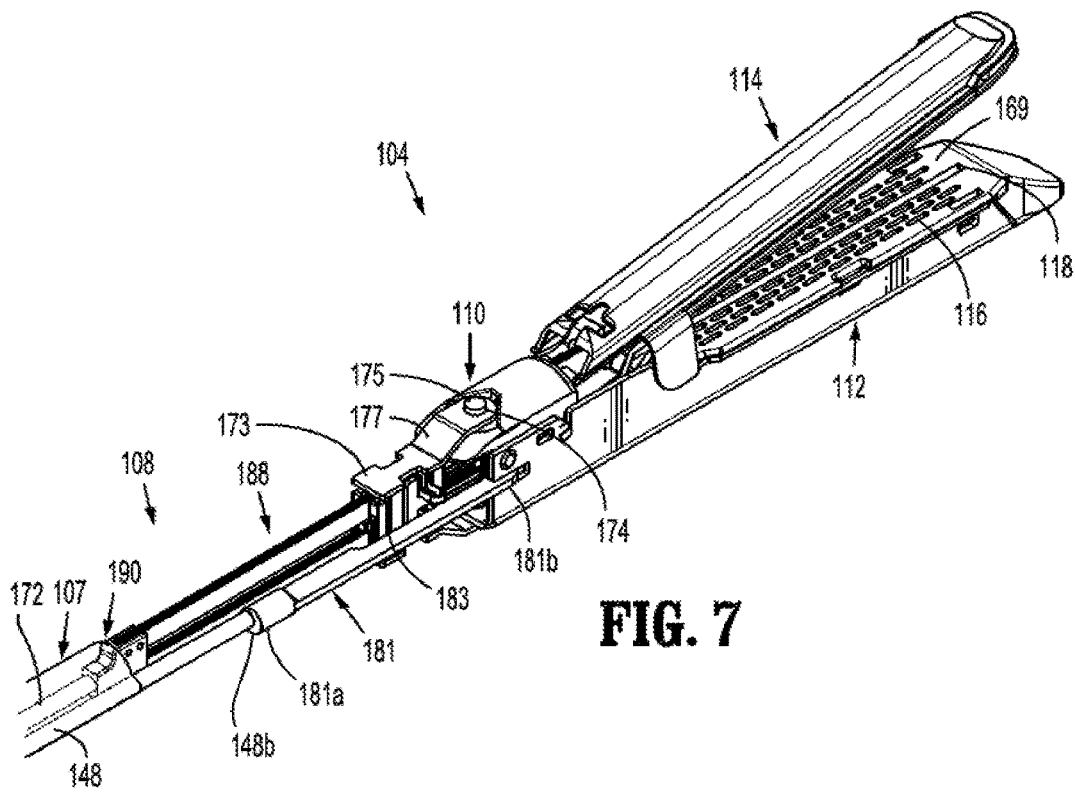
FIG. 7 is a perspective view of the distal portion of the loading unit of FIG. 1.
FIG. 8 is a perspective view of an axial drive assembly according to an embodiment of the present disclosure.
Figure 9:
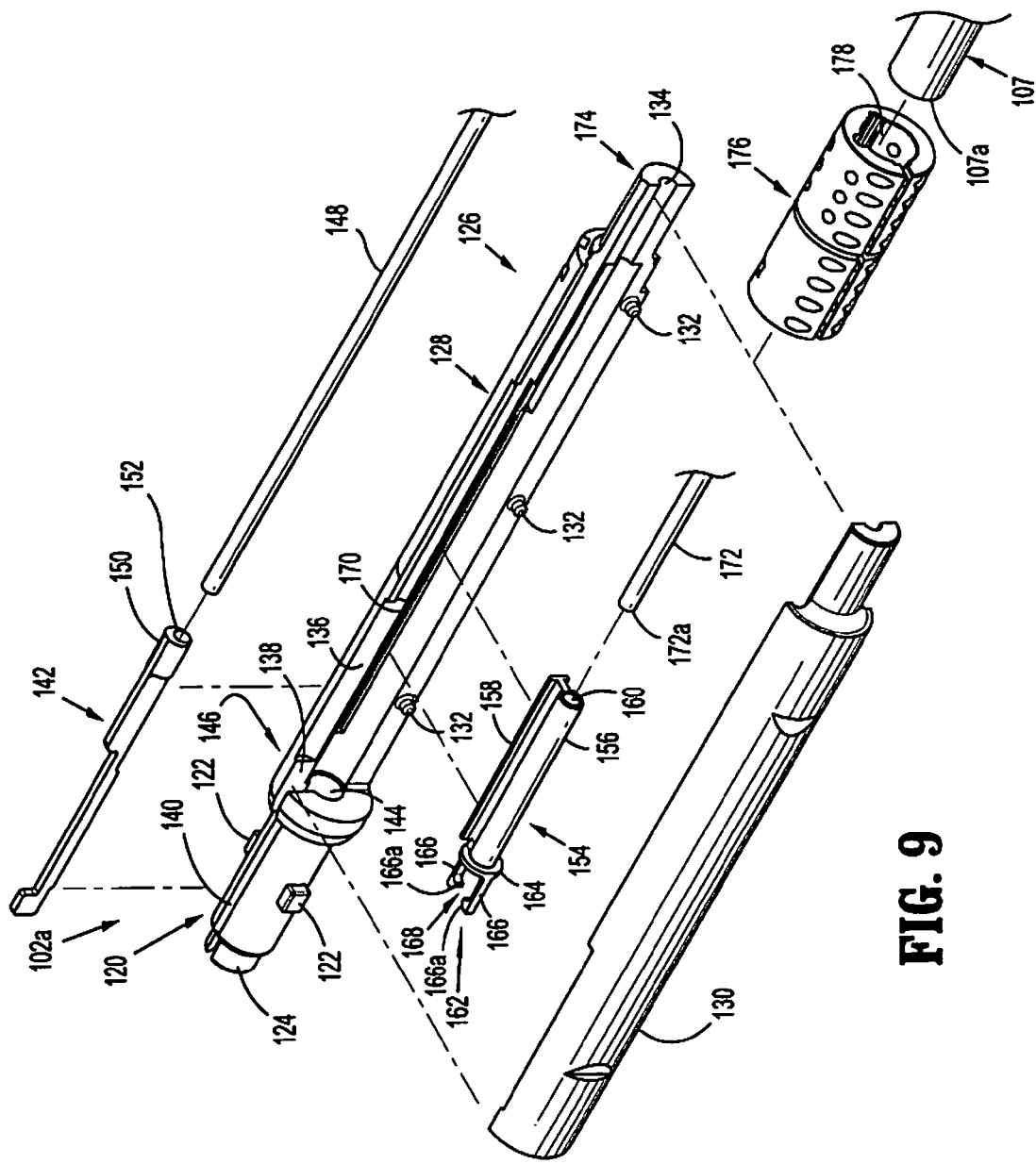
FIG. 9 is a perspective view of the proximal portion of the loading unit of FIG. 1.

With reference to FIGS. 5 and 6, flexible articulation rod 148 is disposed alongside flexible shaft 107. In the depicted embodiment, a holding member 180, such as shrink wrap, holds flexible shaft 107 and flexible articulation rod 148 together. Flexible shaft 107 includes a central lumen 182 configured to receive center rod 172. Thus, flexible shaft 107 surrounds at least a portion of flexible center rod 172. Distal portion 104 of loading unit 100 supports a distal end 107b of flexible shaft 107.

With reference to FIGS. 7, 8, 13, and 15, proximal body 108 of distal portion 104 includes a central bore 184 configured to receive, among other things, distal end 107b of flexible shaft 107. Central bore 184 extends through proximal body 108 and encompasses a coupling member 186, as seen in FIG. 13. Coupling member 186 couples an axial drive assembly 188 to flexible shaft 107 and flexible articulation rod 148. Axial drive assembly 188 has an adapter 190 mounted to its proximal end 188a. Adapter 190 facilitates the interconnection between axial drive assembly 188 and flexible center rod 172. In one embodiment, adapter 190 of axial drive assembly 188 includes a hole 192 adapted to receive flexible center rod 172.

In addition to adapter 190, axial drive assembly 188 includes an elongate drive beam 194 having a distal working head 196. (See FIG. 8.) Drive beam 194 may be constructed from a single sheet material or from multiple stacked sheets. Distal working head 196 has a retention flange 199 and a support strut 197. Retention flange 199 supports at least one cam roller 195 at its distal end. In the embodiment shown in FIG. 8, retention flange 199 supports two cam rollers 195 positioned transversely with respect to retention flange 199. Cam rollers 195 are slidably engaged to anvil assembly 114 such that when axial drive assembly 188 is translated distally, anvil assembly 114 moves from the open position to the clamped position, as depicted in FIG. 18. Support strut 197 has an abutment surface 191 that engages a central portion of an actuation sled 189. In an alternate embodiment, support strut 197 supports a cutting tool. As seen in FIG. 13, support strut 197, which is slidably positioned within cartridge assembly 112, also includes a base 187 adapted to engage a support member 185. Support member 185 of distal working head 196 is located on a lower portion of cartridge assembly 112. In general, the distal working head 196 of elongate drive beam 194 is positioned within cartridge assembly 112. Another portion of elongate drive beam 194, however, is slidably located in central bore 184 of proximal body 108. Proximal body 108 also houses a pair of blow out plates 183 positioned on elongate drive beam 194 of axial drive assembly 188. Blow out plates 183 dampen the bulging of axial drive assembly 188 during articulation and firing of tool assembly 106.

Proximal body 108 also surrounds a portion of flexible articulation rod 148. A distal end 148b of flexible articulation rod 148 is operatively connected to a proximal end 181a of an articulation link 181. A distal end 181b of articulation link 181 is operatively coupled to a projection 179 located on a proximal portion of cartridge assembly 112. Projection 179 is laterally offset from pivot member 110, such that the longitudinal movement of articulation link 181 causes the articulation of tool assembly 106, as described in detail below.

In one embodiment, pivot member 110 has a connecting member 177 and a pivot pin 175. Connecting member 177 includes an interlocking proximal portion 177a for facilitating connection between proximal body 108 and tool assembly 106. A distal portion of connecting member 177 includes an opening 173 adapted to receive pivot pin 175. Although the drawings show a specific kind of pivot member 110, one skilled in the art will envision that any suitable apparatus may pivotably connect proximal body 108 to tool assembly 106.

As discussed hereinabove, tool assembly 106 includes anvil assembly 114 and cartridge assembly 112. Anvil assembly 114, which is configured to move relative to cartridge assembly 112, has a tissue contacting surface 171. Tissue contacting surface 171 includes fastener forming concavities (not shown) adapted to deform fasteners when driven towards anvil assembly 114 from cartridge assembly 112. Cartridge assembly 112 also has a tissue contacting surface 169. Retention slots 116 are arranged in longitudinal rows on tissue contacting surface 169. In the depicted embodiment, cartridge assembly 112 has six longitudinal rows of retentions slots 116. Retention slots 116 also retain pushers (not shown). In operation, actuation sled 189 interacts with pushers to eject the fasteners housed in retention slots 116.

Actuation sled 189 includes at least one cam wedge 167 and is operatively secured to axial drive assembly 188. During firing of tool assembly 106, actuation sled 189 translates through cartridge assembly 112 to advance cam wedges 167 into sequential or simultaneous contact with the pushers. When cam wedges 167 contact the pushers, the pushers translate vertically within retention slots 116 and urge the fasteners from retention slots 116 into the fastener deforming concavities of anvil assembly 114.

Referring now to FIGS. 16-20, before initiating the stapling operation, users should first secure loading unit 100 to a suitable actuation apparatus, such as apparatus 200. In the case of actuation apparatus 200, users may connect actuation apparatus 200 to proximal portion 102 of loading unit 100 by advancing actuation shaft 214 in the direction indicated by arrow "A" until distal protrusion 216 engages legs 166 of locking member 154. Before or after properly connecting an actuation apparatus to proximal portion 102, the user may insert loading unit 100 through a cannula or an incision in a patient. While inserting loading unit 100 into a patient, the user may bend flexible shaft 107 to reach the target surgical site. Also, the user may articulate tool assembly 106 to place it in the desired location. To articulate tool assembly 106, the user should activate the articulation mechanism of the connected actuation apparatus. As the articulation mechanism is triggered, articulation component 142 moves in a proximal or distal direction through slit 140. If the user moves articulation component 142 distally, as indicated by arrows "B" in FIG. 19, articulation rod 148 moves distally, as indicated by arrow "C." The distal translation of articulation rod 148 causes the corresponding distal advancement of articulation link 181 in the direction indicated by arrow "D." As articulation link 181 is advanced distally, tool assembly 106 pivots about pivot member 110 in the direction indicated by arrow "E." To articulate tool assembly 106 in an opposite direction, the user should move articulation component 142 in a proximal direction.

Figure 21:
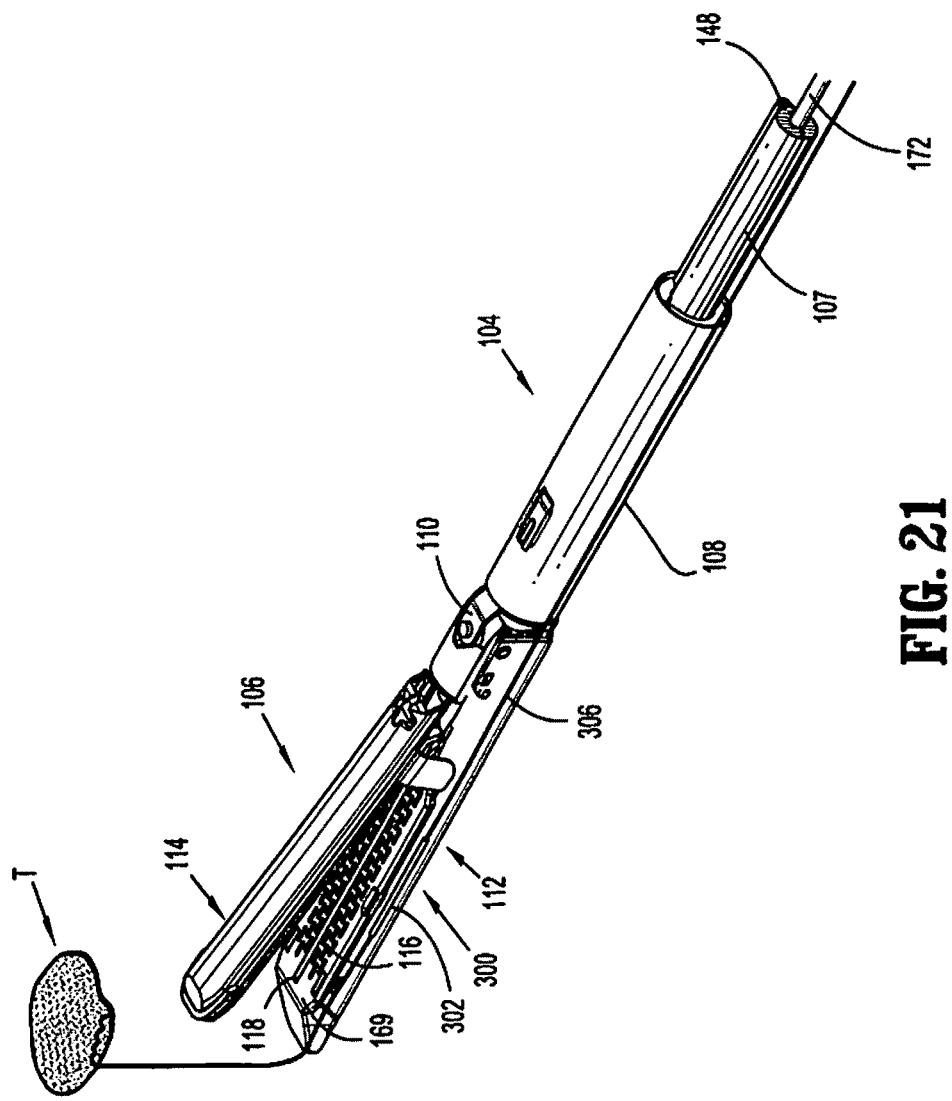
FIG. 21 is a perspective view of the distal portion of the loading unit with a guiding member and a suture stitched to a tissue portion.
Figure 22:
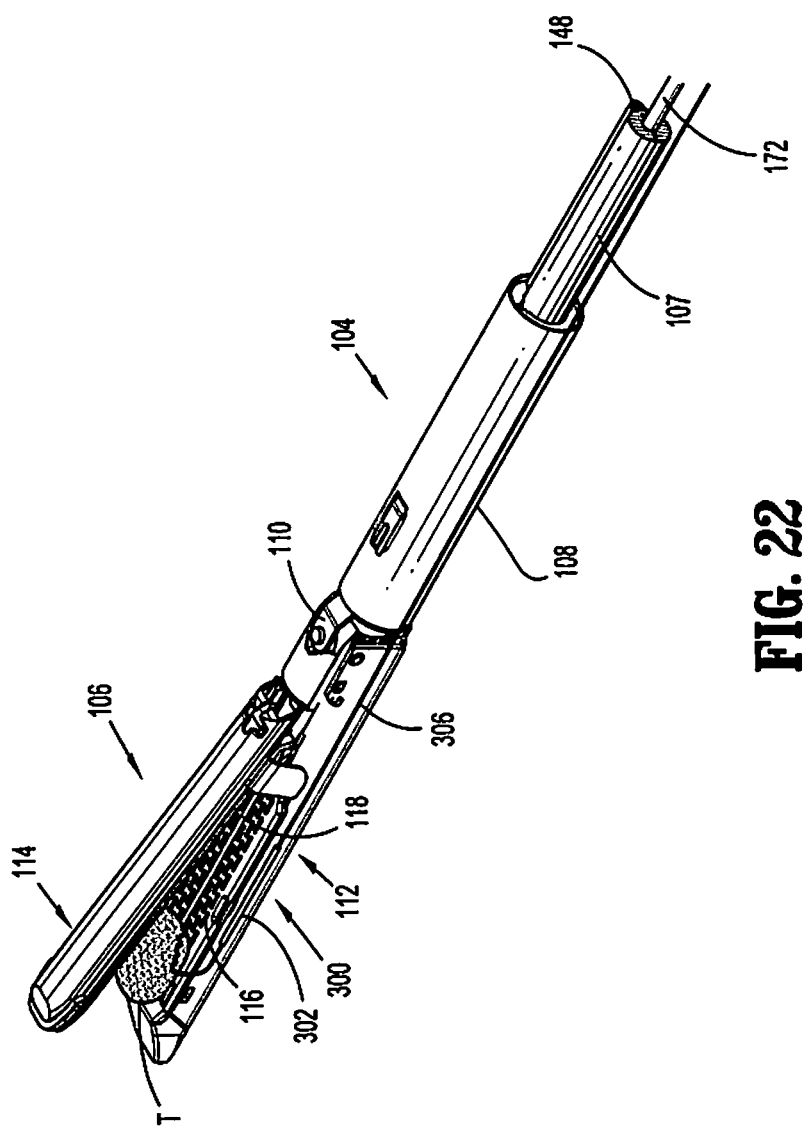
FIG. 22 is a perspective view of the distal portion of the loading unit with a guiding member and a tissue portion positioned between the anvil and cartridge assemblies.

With reference to FIGS. 21 and 22, while using the embodiment depicted in FIG. 3A, a surgeon places tool assembly 106 into the desired surgical site by using guiding member 300. Initially, the surgeon stitches the desired tissue portion T with suture 306, as illustrated in FIG. 21. Then, the surgeon moves loading unit 100 distally. Since suture 306 is slidably positioned in bore 304 of guiding member 300, suture 306 guides the movement of tool assembly 106 as the surgeon advances loading unit 100 distally. As the surgeon moves loading unit 100 in a distal direction, tool assembly 106 moves alongside a portion of the length of suture 306. After approximating tool assembly 106 to the target site, the surgeon pulls suture 306 in a proximal direction to place the tissue portion T between cartridge assembly 112 and anvil assembly 114, as shown in FIG. 22. Given that the tissue portion T is attached to suture 306, the proximal motion of suture 306 causes the corresponding proximal motion of tissue portion T.

After placing tool assembly 106 in the target position, the user may fire tool assembly 106 to fasten tissue. The user may fire tool assembly 106 by triggering an actuation apparatus properly connected to loading unit 100. When the connected actuation apparatus is triggered, locking member 154 moves distally through first bore 134 of proximal portion 102. The distal translation of locking member 154 causes the corresponding distal movement of flexible center rod 172, as indicated by arrows "F." As flexible center rod 172 moves distally, axial drive assembly 188 advances distally in the direction indicated by arrows "G." While axial drive assembly 188 moves distally, cam rollers 195 slide through anvil assembly 114 and move anvil assembly 114 from an open position, as illustrated in FIG. 13, to a clamped position, as depicted in FIG. 18. When anvil assembly 114 moves to its clamped position, it pivots in the direction indicated by arrow "H" in FIG. 18.

The distal advancement of axial drive assembly 188 also causes the corresponding distal movement of actuation sled 189 in the direction indicated by arrow "I." As actuation sled 189 translates through cartridge assembly 112, cam wedges 167 advance and sequentially or simultaneously contact the pushers. When cam wedges 167 contact the pushers, the pushers translate vertically within retention slots 116 and urge the fasteners from retention slots 116 into the fastener deforming concavities of anvil assembly 114.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

What is claimed is:
1. A method of performing a surgical procedure comprising:
    providing a surgical device including a tool assembly and a guiding member operatively secured to the tool assembly, the guiding member having a body defining a bore adapted to slidably receive a suture;
    inserting a portion of the suture through the bore of the body of the guiding member;
    stitching a tissue portion with the suture;
    advancing the surgical device toward the tissue portion;

moving the suture proximally to position the tissue portion near the tool assembly including positioning the tissue portion within the tool assemly; and actuating the tool assembly.

2. The method according to claim 1, wherein advancing the surgical device toward the tissue portion includes moving the surgical device alongside a portion of a length of the suture.

3. The method according to claim 1, wherein actuating the tool assembly includes translating a cutting tool through the tissue portion.

4. A method of performing a surgical procedure comprising:

providing a surgical device including a tool assembly and a guiding member operatively secured to the tool assembly, the guiding member having a body defining a bore adapted to slidably receive a suture;

inserting a portion of the suture through the bore of the body of the guiding member;

stitching a tissue portion with the suture;

advancing the surgical device toward the tissue portion;

moving the suture proximally to position the tissue portion near the tool assembly; and actuating the tool assembly including firing a fastener through the tissue portion.

5. A method of performing a surgical procedure comprising:

affixing a suture to tissue at a desired surgical site;

positioning a portion of the suture within a bore of a guiding member of a tool assembly;

advancing the tool assembly distally, the suture sliding within the bore of the guiding member to guide the tool assembly to the desired surgical site; and pulling the suture in a proximal direction to place the tissue between first and second surfaces of the tool assembly.

6. The method of claim 5 further including firing the tool assembly to fasten the tissue between the first and second surfaces.

7. The method of claim 5, wherein the tool assembly is positioned at a distal end of a loading unit, and the method further includes coupling the proximal end of the loading unit to a proximal end of a surgical instrument.

8. The method of claim 7, wherein the loading unit is flexible such that when the tool assembly is advanced the guiding member flexes the loading unit to guide the tool assembly.

* * * * *